(12) United States Patent
Li

(10) Patent No.: US 6,983,546 B2
(45) Date of Patent: Jan. 10, 2006

(54) DEVICE AND METHOD FOR DETERMINING PARAMETERS OF BLIND VOIDS

(75) Inventor: Lehmann K. Li, Milford, CT (US)

(73) Assignee: SDGI Holdings, Inc., Wilmington, DE (US)

( * ) Notice: Subject to any disclaimer, the term of this patent is extended or adjusted under 35 U.S.C. 154(b) by 18 days.

(21) Appl. No.: 10/827,100

(22) Filed: Apr. 19, 2004

(65) Prior Publication Data

US 2004/0254504 A1 Dec. 16, 2004

Related U.S. Application Data

(63) Continuation of application No. 10/330,699, filed on Dec. 27, 2002, now Pat. No. 6,723,058, which is a continuation of application No. 09/894,727, filed on Jun. 28, 2001, now Pat. No. 6,500,132.

(60) Provisional application No. 60/215,486, filed on Jun. 30, 2000.

(51) Int. Cl.
*A61B 5/107* (2006.01)

(52) U.S. Cl. .................. 33/501.08; 33/511; 33/512; 600/594; 128/898

(58) Field of Classification Search ............... 604/594, 604/587; 33/501.05, 501.08, 511, 512; 128/898
See application file for complete search history.

(56) References Cited

U.S. PATENT DOCUMENTS

| 3,918,164 | A | 11/1975 | Krautmann |
| 5,197,465 | A | 3/1993 | Montgomery |
| 5,471,756 | A | 12/1995 | Bolanos et al. |
| 5,823,974 | A | 10/1998 | Grassi |
| 6,224,599 | B1 | 5/2001 | Baynham et al. |
| 6,500,132 | B1 | 12/2002 | Li |
| 6,723,058 | B2 | 4/2004 | Li |
| 6,729,037 | B2 * | 5/2004 | White ................ 33/512 |

* cited by examiner

*Primary Examiner*—Kevin Lee
(74) *Attorney, Agent, or Firm*—Woodard, Emhardt, Moriarty, McNett & Henry LLP

(57) ABSTRACT

Device for determining the size of a blind void comprises an elongated rigid rod, an actuator slidably movable relative to the rod, the actuator having a distal end for insertion into the void, a distal flexible element fixed at one end thereof to the rod, a second flexible element fixed at one end thereof to the rod and proximally removed from the distal flexible element. Movement of the actuator is operative to cause equal movements of the distal end portions of the distal and proximal elements, to cause the distal element to bulge outwardly from the rod to engage interior walls of the void and to cause the proximal element to bulge outwardly in a configuration duplicative of the distal element bulge, the proximal element being outside of the void and subject to observation.

27 Claims, 4 Drawing Sheets

DEVICE AND METHOD FOR DETERMINING PARAMETERS OF BLIND VOIDS

CROSS REFERENCE TO RELATED APPLICATIONS

This patent application is a continuation of U.S. patent application Ser. No. 10/330,699, filed Dec. 27, 2002, now U.S. Pat. No. 6,723,058 which is a continuation of U.S. patent application Ser. No. 09/894,727, filed Jun. 28, 2001 and issued as U.S. Pat. No. 6,500,132, which claims the benefit of U.S. Provisional Patent Application Ser. No. 60/215,486, filed Jun. 30, 2000, the contents of each application hereby being incorporated herein by reference.

FIELD OF THE INVENTION

This invention relates to the field of surgical devices used primarily for the repair or replacement of human tissue, including, but not limited to, the nucleus pulposus of the spine. The invention further relates to the method of using such devices.

BACKGROUND OF THE INVENTION

The spinal column is a flexible chain of closely linked vertebral bodies. In a normal human spine there are seven cervical, twelve thoracic and five lumbar vertebral bodies. Below the lumbar vertebrae are the sacrum and coccyx. Each individual vertebra has an outer shell of hard, dense bone. Inside the vertebra is a honeycomb of cancellous bone containing red bone marrow. All of the red blood cells and many of the white blood cells are generated inside this cancellous bone, where the blood cells mature before being released into the blood circulation.

The spinal disc serves as a cushion between the vertebral bodies to permit controlled motion. A healthy disc consists of three components: a gelatinous inner core called the nucleus pulposus; a series of overlapping and laminated plies of tough fibrous rings called the annulus fibrosus; and two superior and inferior thin cartilage layers, connecting the disc to the thin cortical bone of the vertebral bodies, called the endplates.

The spinal disc may be displaced or damaged due to trauma or disease, such as a herniation or degenerative disc disease.

A herniated disc may bulge out and compress itself onto a nerve, resulting in lower leg pain, loss of muscle control, or paralysis. To treat a herniated disc, the offending nucleus portions are generally removed surgically.

Disc degeneration gradually reduces disc height, forcing the annulus to buckle, tear or separate radially or circumferentially, and causing persistent and disabling back pain. Degenerative disc disease is generally treated presently by surgically removing the nucleus and fusing the adjacent vertebral bodies to stabilize the joint.

In either case, whether removing a portion of the nucleus or all of the nucleus, these procedures ultimately place greater stress on adjacent discs to compensate for the lack of motion, which may cause premature degeneration of those adjacent discs.

Modern trends in surgery include the restoration of bodily function and form (i.e., repair) of anatomical structures through the use of minimally invasive surgical techniques. The ability to surgically repair damaged tissues or joints, creating as few and as small incisions as possible, produces less trauma, less pain and better clinical outcomes in general.

An emerging technique to treat degenerative disc disease is to replace the degenerated nucleus with a prosthetic nucleus in an attempt to restore function, versus fusion which severely limits the function of the spine. Since a degenerated nucleus can be removed using relatively small diameter instruments (e.g. 5 mm or less), this approach is more conducive to minimally invasive techniques.

A deficiency of current minimally invasive surgical techniques to replace the nucleus is the difficulty in determining whether enough space in the disc has been created to properly fit an implant. Creating the proper dimension cavity may be particularly important when implanting a device that expands, such as with a hydrogel implant. If the cavity created is larger than the implant, unintended implant movement or instability can occur. If the cavity created is smaller than the implant, an implant either may not fit, may not be positioned correctly or an expandable device may not achieve its proper functional shape.

SUMMARY OF THE INVENTION

It is, therefore, one object of the present invention to provide a device and method for determining how much space is created in human tissue, particularly when the space is in a visually impaired location.

A further object of the invention is to provide a device and method for determining how much space is created in the inner portion of the intervertebral disc space to facilitate the implantation of an artificial nucleus pulposus. The present invention is adapted to be placed through a small opening created in the annulus to minimize trauma to surrounding tissue.

With the above and other objects in view, a feature of the invention is the provision of a device for determining parameters of a blind void. The device comprises an elongated rigid rod, and an actuator extending lengthwise of the rod and slidably movable relative to the rod, the actuator having a distal end for insertion into the void. A first flexible element is fixed at one end thereof to the rod proximate the distal end of the rod. A second flexible element is fixed at one end thereof to the rod and proximally removed from the distal end of the rod and from the first element. Movement of the actuator is operative to cause equal movements of the distal end portions of the first and second elements, to cause the first element to bulge outwardly from the rod to engage interior walls of the void and to cause the second element to bulge outwardly in a configuration substantially duplicative of the first element bulge, the second element being outside of the void and subject to observation.

In accordance with a further feature of the invention, there is provided a method for determining parameters of a blind void, the method comprising the steps of providing a device comprising an elongated rigid rod, a first flexible element fixed at one end thereof to the rod proximate a distal end of the rod, a second flexible element fixed at one end thereof to the rod and proximally removed from the distal end of the rod and from the first element, and an actuator extending lengthwise of the rod and engageable with distal end portions of the first and second elements. The method further includes the steps of inserting the distal end of the actuator and the first element into the void, moving the actuator to cause movements of the distal end portions of the first and second elements, to cause the first element to bulge outwardly to engage interior walls of the void, and to cause the second element to bulge outwardly in a configuration duplicative of the first element bulge, the second element being outside of the void, and determining from the size of the second element the size of the first element and thereby the void.

The above and other features of the invention, including various novel details of construction and combinations of parts and method steps, will now be more particularly described with reference to the accompanying drawings and pointed out in the claims. It will be understood that the particular device and method embodying the invention are described by way of illustration only and not as limitations of the invention. The principles and features of this invention may be employed in various and numerous embodiments without departing from the scope of the invention.

BRIEF DESCRIPTION OF THE DRAWINGS

Reference is made to the accompanying drawings in which is shown an illustrative embodiment of the invention, from which its novel features and advantages will be apparent.

In the drawings.

DETAILED DESCRIPTION OF THE PREFERRED EMBODIMENTS

Figure 1:
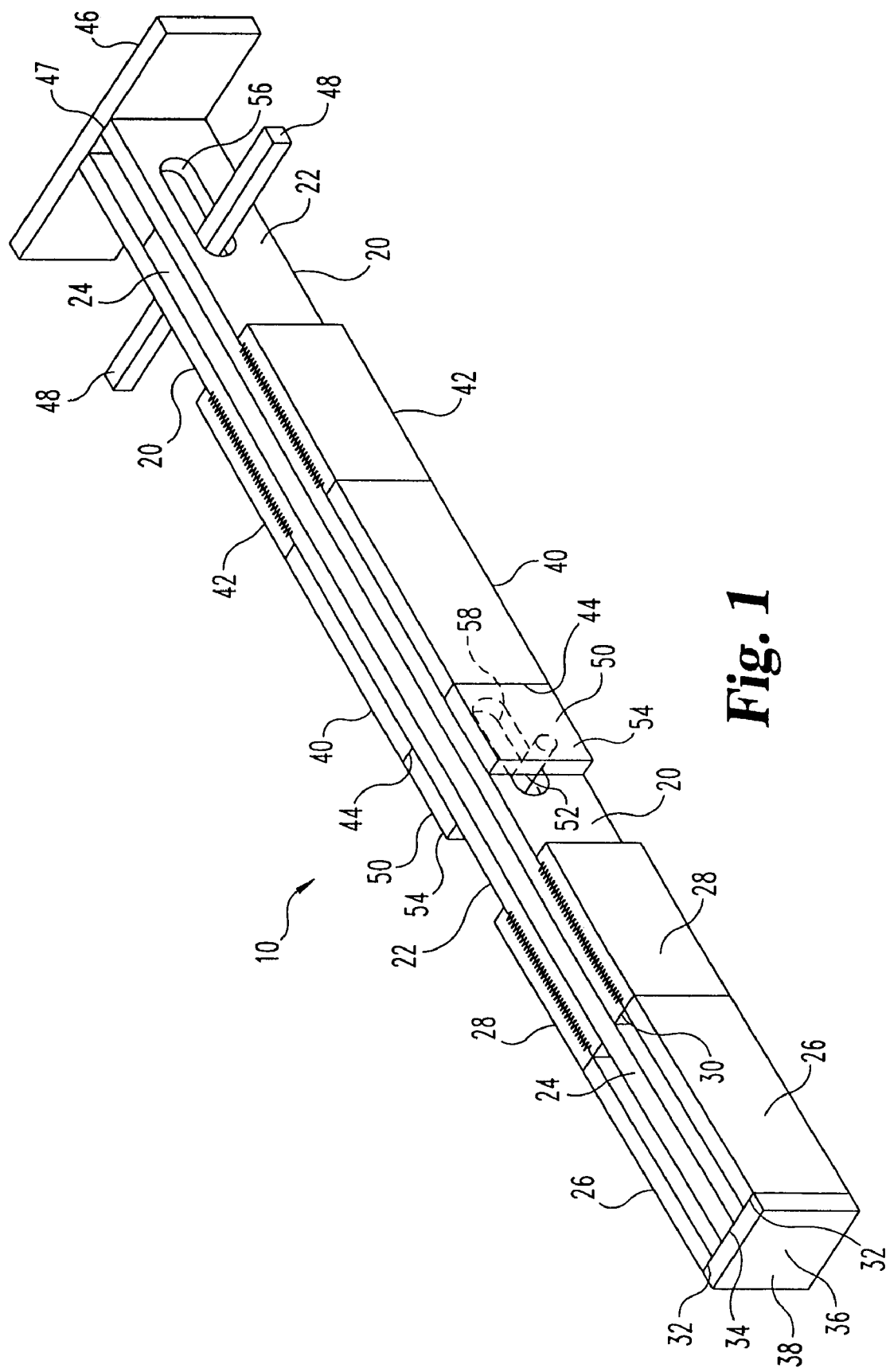
FIG. 1 is a perspective view of one form of device illustrative of an embodiment of the invention.

Referring to FIG. 1, it will be seen that an illustrative inventive device 10 includes an elongated rigid rod 20, in the form of at least one, and preferably two, plates 22. When the device includes two plates, the plates extend parallel to each other.

An actuator 24 extends lengthwise of the rod 20 and is slidably movable relative to the rod 20. When the rod 20 includes two plates 22, the actuator 24 is slidably disposed between the two plates.

A first flexible element, such as a strip 26, is fixed at a proximal end portion 28 thereof to the rod 20 proximate the distal end 30 of the rod. The element 26 may be a bendable strip of metal having a distal free end 32. A first flexible element 26 is fixed to each of the plates 22.

Mounted on a distal end 34 of the actuator 24 is a first engagement member 36 which is engageable with the distal end 32 of each of the first elements 26. The first engagement member 36 may be an end-piece 38 fixed to the distal end 34 of the actuator 24.

A second flexible element, such as a strip 40, is fixed to each of the plates 22 at a proximal end portion 42 of the element. The element 40 is of the same configuration, size and material as the element 26 and is provided with a distal free end 44. A flexible second element 40 is fixed to each of the plates 22 proximally of the distal end 30 of the rod 20 and proximally of the first flexible element 26.

Mounted on each of the plates 22 on a side opposite from the actuator 24 is a second engagement member 50 connected to the actuator 24 by a connecting pin 52. The second engagement member 50 may be a block 54.

The rod 20 is provided with a grip portion 46 at the proximal end 47 of the rod by which the rod may be gripped by an operator (not shown). The actuator 24 is provided with a manipulable portion, such as a cross-bar 48, such that an operator may hold the device 10 in one hand by gripping the rod grip portion 46 and the actuator cross-bar 48, and by squeezing the cross-bar toward the grip portion, cause the actuator to move proximally relative to the plates 22. The plates are each provided with a slot 56 through which extends a cross-bar portion, such that the cross-bar 48 may readily move relative to plates 22. Similarly, the plates 22 are each provided with a slot 58 through which extends the connecting pin 52, permitting movement of the engagement block 54 relative to the plates 22.

Figure 2:
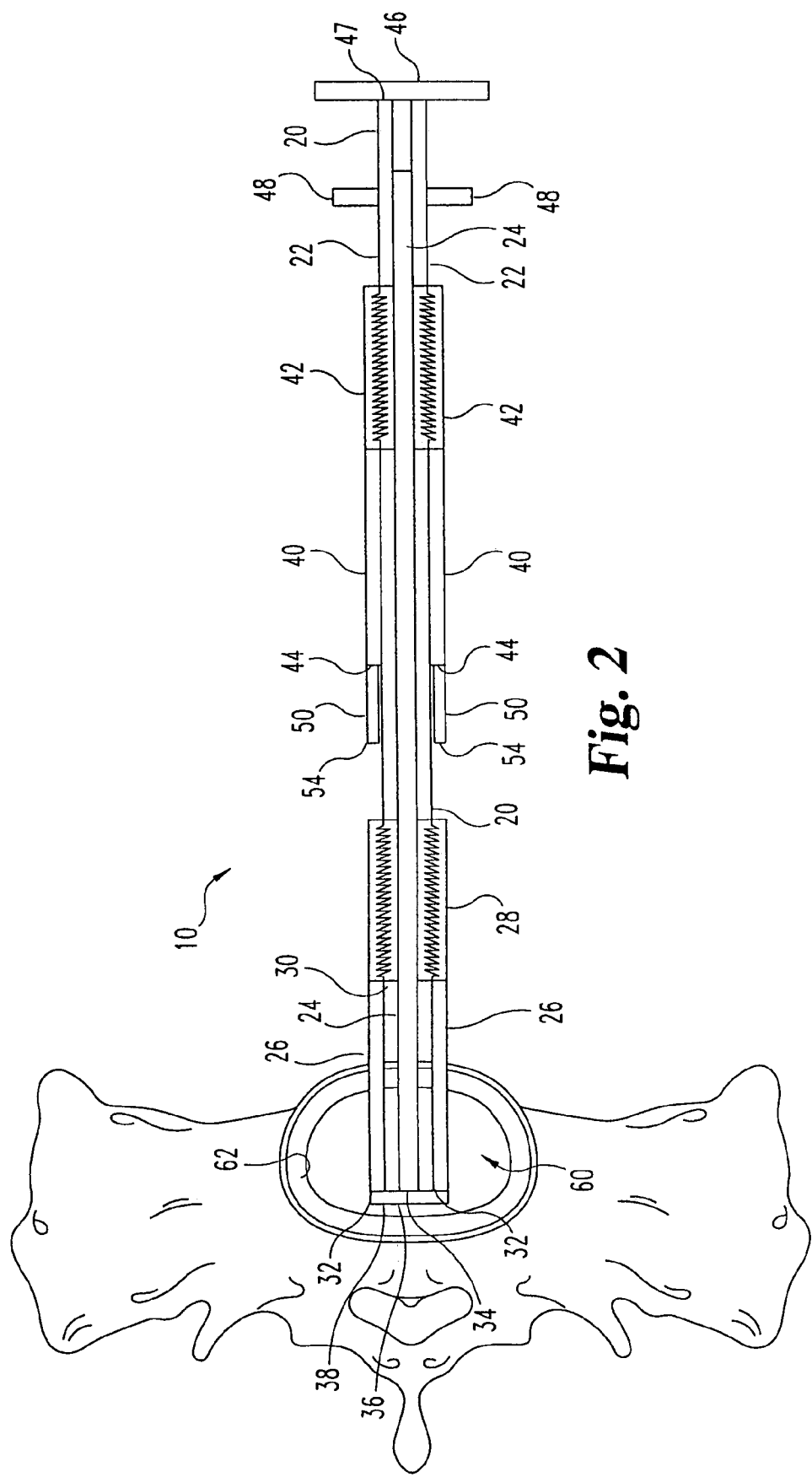
FIG. 2 is a diagrammatic top view of the device of FIG. 1 deployed in a spinal disc.
Figure 3:
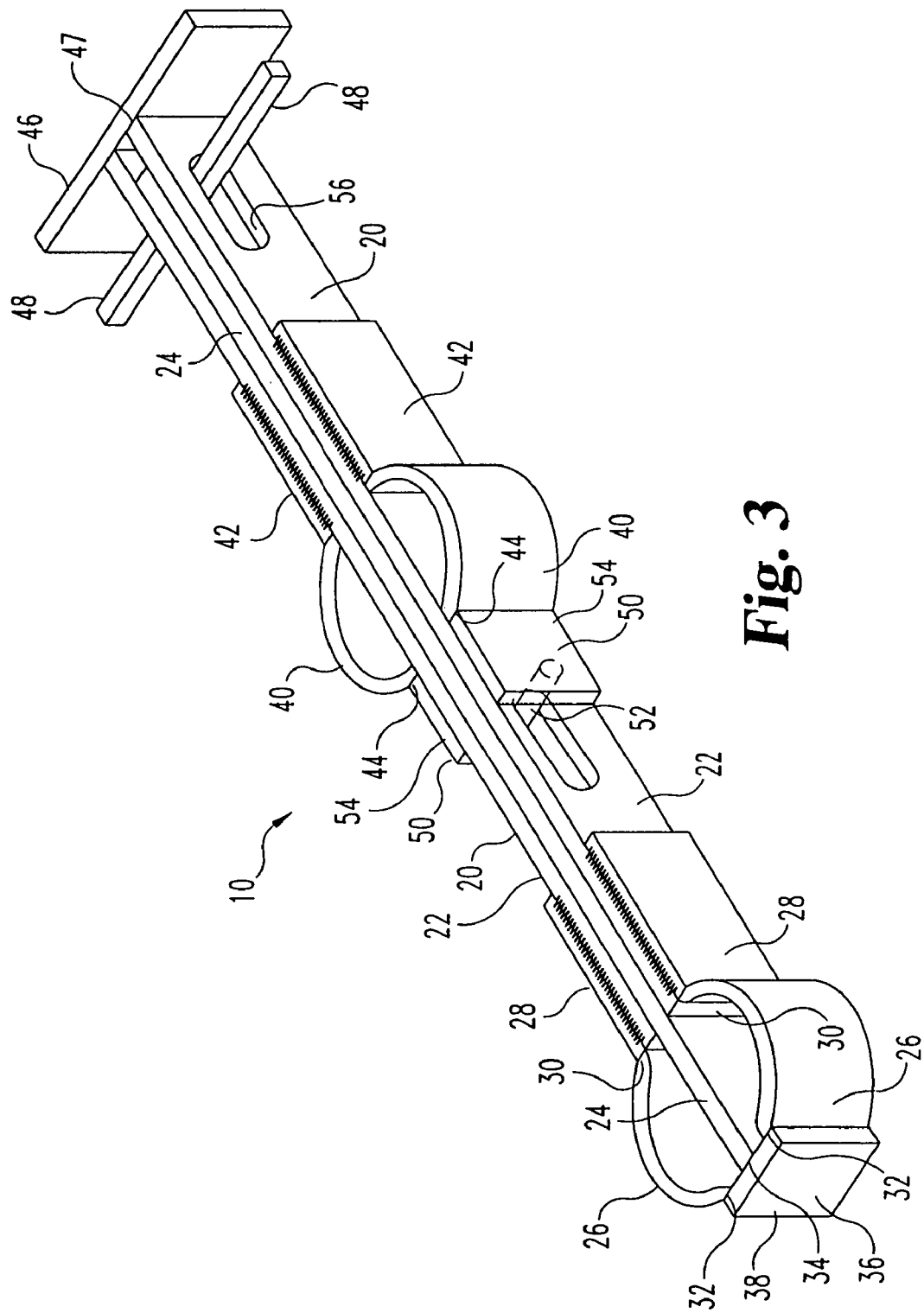
FIG. 3 is similar to FIG. 1, but shows the device in another operative configuration.
Figure 4:
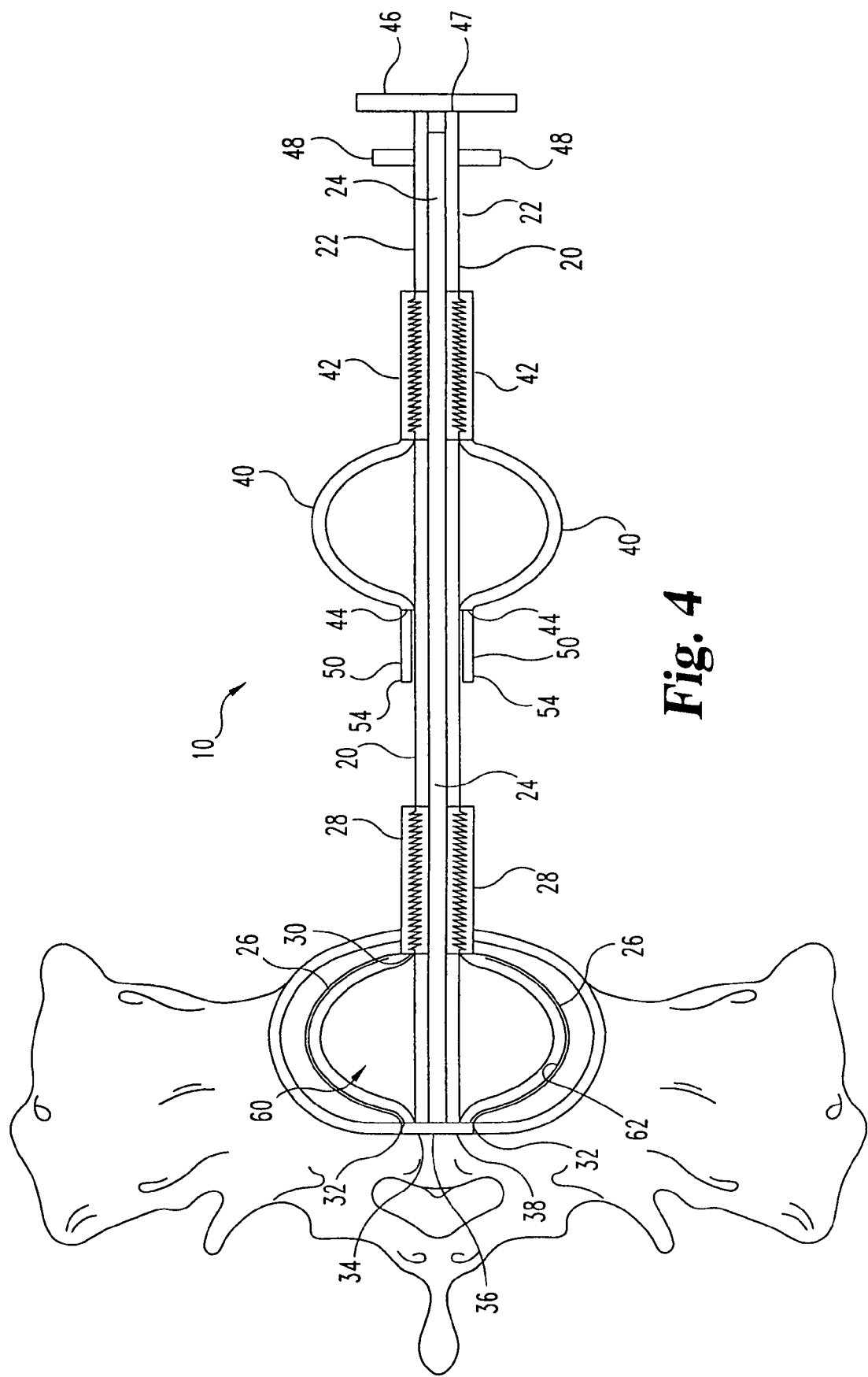
FIG. 4 is similar to FIG. 2, but shows the device in a parameter determining configuration.

In operation, the device 10, as shown in FIG. 1, is inserted into a void, such as a spinal disc cavity 60 from which the nucleus pulposus has been removed (FIG. 2). By manipulation of the rod grip portion 46 and actuator cross-bar 48, the actuator 24 is made to move proximally relative to the rod 20. Proximal movement of the actuator 24 carries with it proximal movement of the end piece 38 and engagement block 54 which, contacting the element free distal ends 32,44, respectively, cause proximal movement of the flexible element free ends 32,44, while the flexible element proximal ends 28,42 remain fast to their respective plates 22. The elements are thus caused to bulge outwardly (FIGS. 3 and 4) until the first element 26 engages interior walls 62 of the cavity 60, stopping movement of the actuator 24.

At this point, the first element 26 is hidden from view and the extent of the bulge is not ordinarily observable. However, because the second flexible element 40 is of the same configuration, size and material as the first element and expands in a manner duplicating the expansion of the first element, and is in an observable disposition, the size of the spinal disc cavity may be determined by observation of the second element. While it is intended that "observation" includes visual observation and mechanical measurement, it is apparent that "observation" can be undertaken by optical or automatic data gathering instruments in combination with computers and/or read-out devices.

It should also be appreciated that device 10 may be used to determine cavity sizes in a variety of different directions. Thus, for example, in FIGS. 2–4, device 10 is shown oriented so as to measure cavity size in a substantially horizontal direction. However, it should also be appreciated that device 10 may be oriented, or modified, so as to measure cavity size in a substantially vertical direction, or in some other direction.

There is thus provided a device and method for determining the space available in a blind void, and particularly in a spinal disc cavity vacated by extraction of the nucleus pulposus therefrom.

It is to be understood that the present invention is by no means limited to the particular construction herein disclosed and/or shown in the drawings, but also comprises any modification or equivalent within the scope of the claims.

What is claimed is:

1. A device for determining a parameter of a blind void, comprising:
    a first element adapted for insertion within the blind void and for transitioning to a first configuration corresponding to a parameter of the blind void;
    a second element adapted for disposition outside of the blind void; and
    an actuator device coupled between said first and second elements to transition said second element to a second configuration relating to said first configuration of said first element.

2. The device of claim 1, wherein each of said first and second elements are at least partially formed of a flexible material.

3. The device of claim 2, wherein each of said first and second elements comprises at least one flexible strip of material.

4. The device of claim 3, wherein said first and second configurations of said first and second elements are defined by an outward deformation of said at least one flexible strip of material.

5. The device of claim 4, wherein said outward deformation comprises outward buckling of said at least one flexible strip of material.

6. The device of claim 3, wherein each of said first and second elements comprises a pair of said flexible strips of material arranged generally opposite one another.

7. The device of claim 1, wherein said first configuration of said first element engages an interior wall surrounding the blind void.

8. The device of claim 1, wherein said first element has an initial configuration adapted for insertion into the blind void in a minimally invasive manner.

9. The device of claim 1, wherein said second configuration of said second element is substantially identical to said first configuration of said first element.

10. The device of claim 1, wherein said second configuration of said second element is subject to direct visualization.

11. The device of claim 1, wherein said actuator device comprises:
   a first actuator portion coupled between each of said first and second elements; and
   a second actuator portion coupled between each of said first and second elements; and
   wherein relative displacement between said first and second actuator portions transitions said first element toward said first configuration and said second element toward said second configuration.

12. A device for determining a parameter of a blind void, comprising:
   a first element insertable within the blind void and transitionable to a first configuration corresponding to a parameter of the blind void;
   a second element positionable outside of the blind void; and
   an actuator device coupled between said first and second elements to transition said second element to a second configuration corresponding to said first configuration of said first element.

13. The device of claim 12, wherein each of said first and second elements are at least partially formed of a flexible material.

14. The device of claim 12, wherein said second configuration of said second element is substantially identical to said first configuration of said first element.

15. A method for determining a parameter of a blind void, comprising:
   providing a device comprising a first element adapted for insertion within the blind void and a second element adapted for disposition outside of the blind void;
   inserting the first element into the blind void;
   transitioning the first element to a first configuration corresponding to a parameter of the blind void; and
   transitioning the second element to a second configuration relating to the first configuration of the first element.

16. The method of claim 15, wherein at least a portion of each of the first and second elements is at least partially formed of a flexible material; and
   wherein the transitioning comprises flexibly deforming the at least a portion of each of the first and second elements.

17. The method of claim 16, wherein the flexibly deforming comprises outward buckling.

18. The method of claim 15, wherein said first element has an initial configuration sized smaller than the first configuration; and
   further comprising inserting the first element into the blind void in a minimally invasive manner while in the initial configuration.

19. The method of claim 18, further comprising:
   transitioning the first element back toward the initial configuration; and
   removing the first element from the blind void.

20. The method of claim 15, wherein the transitioning of the first element to the first configuration comprises engaging the first element against an interior wall surrounding the blind void.

21. The method of claim 15, wherein the second configuration of the second element is substantially identical to the first configuration of the first element.

22. The method of claim 15, further comprising observing the second configuration of the second element to determine the approximate configuration of the blind void.

23. The method of claim 22, further comprising:
   selecting an artificial implant having a configuration substantially corresponding to the approximate configuration of the blind void; and
   inserting the artificial implant into the blind void.

24. The method of claim 22, wherein the observing comprises direct visual observation.

25. The method of claim 22, wherein the observing comprises electronic observation.

26. The method of claim 25, wherein the electronic observation comprises automatic data gathering and readout.

27. The method of claim 15, further comprises an actuator element comprising a first actuator portion coupled between each of the first and second elements and a second actuator portion coupled between each of the first and second elements; and
   further comprising displacing the first actuator portion relative to the second actuator portion to facilitate the transitioning of the first and second elements to the first and second configurations.

* * * * *